(12) United States Patent
Düring

(10) Patent No.: US 7,319,020 B1
(45) Date of Patent: Jan. 15, 2008

(54) METHOD FOR CARRYING OUT THE CONTROLLED POST-HARVEST PRODUCTION OF PROTEINS IN HOST ORGANISMS

(75) Inventor: Klaus Düring, Vorgebirgsweg 33, D-50226, Frechen-Königsdorf (DE)

(73) Assignee: Klaus During, Frechen (DE)

( * ) Notice: Subject to any disclaimer, the term of this patent is extended or adjusted under 35 U.S.C. 154(b) by 21 days.

(21) Appl. No.: 09/889,686

(22) PCT Filed: Sep. 5, 2000

(86) PCT No.: PCT/DE00/03119

§ 371 (c)(1),
(2), (4) Date: Nov. 28, 2001

(87) PCT Pub. No.: WO01/38508

PCT Pub. Date: May 31, 2001

(30) Foreign Application Priority Data

Nov. 23, 1999 (DE) ................................ 199 56 272

(51) Int. Cl.
*C12N 15/82* (2006.01)
*C12N 15/63* (2006.01)
*C12N 5/04* (2006.01)

(52) U.S. Cl. .................. 435/69.1; 435/320.1; 435/468; 536/24.1; 800/278; 800/317.2

(58) Field of Classification Search ................. 800/288, 800/295, 298, 306, 312, 317.2, 320.1; 435/320.1
See application file for complete search history.

(56) References Cited

U.S. PATENT DOCUMENTS 5,670,349 A    9/1997 Cramer et al.
6,194,201 B1 *  2/2001 Cerff et al. ............... 435/320.1

FOREIGN PATENT DOCUMENTS

| AU | 724617 | 9/1997 |
| EP | 0278658 A3 | 8/1988 |
| WO | WO 95/00555 | 1/1995 |
| WO | WO 95/00555 A1 * | 1/1995 |
| WO | WO 95/03690 | 2/1995 |
| WO | WO 97/22707 | 6/1997 |

OTHER PUBLICATIONS

Gatz, Chemical Control of Gene Expression, Annu. Rev. Plant Physiol. Mol. Biol., vol. 48, pp. 89-108, 1997.*

Kohler et. al. A promoter for strong and ubiquitous anaerobic gene expression in tobacco, The Plant Journal, vol. 10, pp. 175-183, 1996.*
Imhof, et al. J. Clinical Microbiology, Jul. 1996, pp. 1646-1648. submitted by Applicant Jan. 23, 2006.*
(Raven et al, Biology of Plants (1992), Worth Publishers, New York, NY 10003, p. 382, Table 18, and 494-5, Figures 23-8, 23-9 and 23-10).*
Walton, P. in Principles and Practice of Plant Science, 1988, published by Prentice Hall, New Jersey, pp. 397-400.*
Fehr, W, in Principles of Cultivar development, vol. 1, 1987, published by McGraw-Hill, p. 62.*
Germain, et al.; "The Role of Sugars, Hexokinase, and Sucrose Synthase in the Determination of Hypoxically Induced Tolorance to Anoxia in Tomato Roots"; Plant Physiol. (1997) 114: 167-175.
Aoyama, et al., "A Glucocorticoid-Mediated Transcriptional Induction System in Transgenic Plants", *Plant J.*, 11(3): 605-12 (1997).
Brown, et al., "Requirements for the Translational Repression of Ferritin Transcripts in Wheat Germ Extracts by a 90-kDa Protein from Rabbit Liver", *J. of Biol. Chem.*, 264(23): 13383-6 (1989).
Bülow, et al., "Induction of the Maize GapC4 Promoter in Transgenic Potato Under Anaerobiosis and in *Erwinia carotovora*-Inoculated Tuber Tissue", *Molecular Plant-Microbe Interactions*, MPMI 12(3): 182-8 (1999).
Caddick, et al., "An Ethanol Inducible Gene Switch for Plants Used to Manipulate Carbon Metabolism", *Nature Biol.*, 16: 177-80 (1998).
Gatz, "Chemical Control of Gene Expression", *Annu. Rev. Plant Physiol. Plant Mol. Biol.*, 48: 89-108, (1997).
Gatz, et al., "Promoters That Respond To Chemical Inducers", *Reviews*, 3(9): 352-8 (1998).
Martinez, et al., "Ecdysone Agonist Inducible Transcription in Transgenic Tobacco Plants", *Plant J.*, 19(1): 97-106 (1999).
Raventós, et al., "HRT A Novel Zinc Finger, Transcriptional Repressor From Barley", *J. of Biol. Chem.*, 273(36): 23313-20 (1998).

* cited by examiner

Primary Examiner—Russell P. Kallis
Assistant Examiner—Brent T Page
(74) Attorney, Agent, or Firm—Howrey LLP; Viola T. Kung

(57) ABSTRACT

The invention relates to a method of obtaining a desired protein from a transgenic host organism, the gene coding for this protein being not expressed until the host organism has been harvested and the method being characterized in that (a) the transgenic host organism contains the gene coding for the desired protein such that it is only expressed in the presence of a chemical inductor, and (b) contacting with the inductor takes place via the phase surrounding the host organism after the host organism has been harvested. The invention also relates to a host organism suitable for carrying out this method.

2 Claims, No Drawings

SEQUENCE LISTING

<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Primer -continued

<400> SEQUENCE: 1
catgtcaaca cataaggaag aagaggtaga aag                33

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
catgccatgg atcgatgacg gggttggcga gtgtg              35

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
catgccatgc cacaatttga tatattatgt aaaac              35

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
gctctagatc agactgtggc agggaaaccc tc                 32

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
ccatgccatg ccacaatttg atatattatg taaaac             36

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
gctctagatc agactgtggc agggaaaccc tc                 32

METHOD FOR CARRYING OUT THE CONTROLLED POST-HARVEST PRODUCTION OF PROTEINS IN HOST ORGANISMS

This application is a National Stage of International Application PCT/DE00/03119, filed Sep. 5, 2000; which claims the priority of DE 199 56 272.5, filed Nov. 23, 1999. The present invention relates to a method of obtaining a desired protein from a transgenic host organism, the gene coding for this protein being not expressed until the host organism has been harvested and the method being characterized in that said gene is only expressed in the presence of a chemical inductor supplied after the harvest of the host organism thereto via the surrounding phase, in particular gas or liquid phase.

The present invention relates to a method of obtaining a desired protein from a transgenic host organism, the gene coding for this protein being not expressed until the host organism has been harvested and the method being characterized in that said gene is only expressed in the presence of a chemical inductor supplied after the harvest of the host organism thereto via the surrounding phase, in particular gas or liquid phase.

Proteins occurring in nature are often available in only very small amounts, nevertheless their characteristics for use as active substances and materials are highly interesting. Since they can often also be obtained in recombinant host systems, e.g. bacteria, such as *Escherichia coli, Bacillus subtilis*, etc., in non-efficient manner regarding the economical conditions and sufficient amounts, a commercial application cannot be realized in such cases. In order to be able to produce more and more complex proteins which are hard to produce, or cannot be produced at all, in low organisms, an increasing number of cells of higher organisms with their inherent complex protein biosynthesis machinery is additionally required as host cells. Transgenic animals, plants, fungi, moss, algi, etc., have offered themselves as new recombinant host in this case for some years now. Since the number of well characterized available proteins from molecular research increases constantly, this technology is gaining significance as regards their application.

However, the expression of foreign proteins may have negative effects on the physiological constitution of the host organism, and e.g. impair its growth or even prevent it. In addition it is conceivable that e.g. if transgenic plants expressing medically active proteins are cultivated, these represent a danger potential for organisms in the environment while the plants grow. Therefore, the post-harvest production of foreign proteins in transgenic host organisms, in particular those which are cultivated by means of agriculture or horticulture, is of great significance as a technological building block towards an economical and environmentally compatible extraction of proteins. Other (bio) chemical substances can also be prepared in transgenic host organisms by the expression of enzymes involved in the biosynthesis route thereof. However, this also involves the risk of negative effects on the host organisms, e.g. growth inhibitions, or as regards the biological safety. Since the production of (bio)chemical substances in host organisms is also based on the expression of proteins, in particular enzymes, the same technological standards apply here as well.

Only post-harvest production systems have been described thus far which are based on the wounding of plant material, e.g. in the case of tobacco plants, by comminuting their leaves. As a result, the desired protein shall not yet be produced while the tobacco plant is grown in the field but only after the harvest prior to the recovery step. However, this is difficult to realize, since a wounding-inducible promoter is induced in transgenic plants in agricultural or horticultural cultivation, e.g. in tobacco, already in the case of damage caused by feeding, wind or hail, impact, use of machines, etc. The uniform distribution, which is hard to achieve, of the induction stimulus over the entire plant substance to be induced is another disadvantage of the former method.

Thus, the present invention is based on the technical problem of providing a post-harvest production system for a desired protein which does not have the drawbacks of the method described in the prior art, i.e. ensures above all that gene expression takes place reliably only after the harvest, comminution of the plant tissue is not necessary and the inductor is contacted efficiently and uniformly with the cells of the corresponding transgenic host organism.

This technical problem is solved by the method defined in the claims according to the invention.

In the method according to the invention the expression of a foreign gene is induced in a host organism by a chemical inductor administered via the phase surrounding the host organism. This phase may be a gas or liquid phase, wherein in the former phase the chemical induction may take place by changing the composition of the gas phase, preferably an anaerobic induction, an atomization of solutions (suspensions) of solid or liquid inducing (bio)chemicals or a use of volatile substances and their uniform distribution in the reaction chamber. Furthermore, the chemical induction may take place in the liquid phase via solutions of solid or liquid inducing (bio)chemicals. High-quality proteins or other (bio)chemical substances can be produced by the method according to the invention on a large scale and thus for new (bio)medical and technological fields of application.

Thus, the present invention comprises a method of obtaining a desired protein from a transgenic host organism, the gene coding for this protein being expressed only after the harvest of the host organism and the method being characterized in that (a) the transgenic host organism contains the gene coding for the desired protein such that it is only expressed in the presence of a chemical inductor; and (b) contacting with the chemical inductor takes place after the harvest of the host organism via the phase surrounding the host organism, in particular gas or liquid phase.

A person skilled in the art is familiar with methods of constructing the nucleic acid constructs required for carrying out the method according to the invention, and these methods are also described in common standard works (cf. e.g. Sambrook et al., 1989, Molecular Cloning, A Laboratory Manual, $2^{nd}$ edition, Cold Spring Harbor Laboratory Press, Cold Spring Harbor, N.Y.). The nucleic acid construct is preferably available in that it is inserted on a vector, the vector being preferably a plasmid, a cosmid, a virus, a bacteriophage, or another vector common in genetic engineering. These vectors may have further functional units which stabilize the vectors in the host organism, such as a bacterial replication origin or the 2-mikron-DNA for stabilization in *Saccharomyces cerevisiae*. "Left border" and "right border" sequences of agrobacterial T-DNA may also be contained so as to enable stable integration into the genotype of plants. A termination sequence may also be present which serves for properly terminating the transcription and adding a Poly-A sequence to the transcript. Such elements are described in the literature (cf. Gielen et al., EMBO J. 8 (1989), 23-29) and can be exchanged as desired.

For preparing the insertion of a foreign gene in higher plants a large number of cloning vectors are available which contain a replication signal for *E. coli* and a marker gene for the selection of transformed bacterial cells. Examples of such vectors are pBR322, pUC series, M13 mp series pACYC184, etc. The foreign gene may be inserted in the vector at a suitable restriction site. The resulting plasmid is used for the transformation of *E. coli* cells. Transformed *E. coli* cells are cultured in a suitable medium, then harvested and lyzed so as to obtain the plasmid. In general restriction analyses, gel electrophoreses and further biochemical and molecular-biological methods are used as an analysis method for characterizing the obtained plasmid DNA. Following every manipulation, the plasmid DNA may be cleaved and extracted DNA fragments may be linked with other DNA sequences. Each plasmid DNA sequence may be cloned in the same or other plasmids.

A plurality of techniques are available for the insertion of DNA, e.g. in a vegetable host cell. These techniques comprise the transformation of plant cells with T-DNA using *Agrobacterium tumefaciens* or *Agrobacterium rhizogenes* as the transformation agent, the fusion of protoplasts, the injection, the electroporation of DNA, the insertion of DNA by means of biolistic methods and further possibilities.

For the injection and electroporation of DNA in plant cells no special demands are made on the plasmids used. It is possible to use simple plasmids, e.g. pUC derivatives. However, if whole plants are regenerated from such transformed cells, a selectable marker should be present. Depending on the method of inserting desired genes in the plant cell, further DNA sequences may be necessary. For example, if the Ti or Ri plasmid is used for the transformation of the plant cell, at least the right border, but often the right and left borders, of the Ti and Ri plasmid T-DNA have to be connected as a flanking region with the genes to be inserted.

If *agrobacteria* are used for the transformation, it is favorable to clone the DNA to be inserted in special plasmids, in particular in an intermediary or in a binary vector. The intermediary vectors may be integrated due to sequences which are homologous to sequences in the T-DNA, by homologous recombination in the Ti or Ri plasmid of the *agrobacteria*. This plasmid additionally contains the vir region necessary for the transfer of the T-DNA. Intermediary vectors cannot replicate in *agrobacteria*. The intermediary vector can, by means of the helper plasmid, be transferred to *Agrobacterium tumefaciens*. Binary vectors may replicate in both *E. coli* and *agrobacteria*. They contain a selection marker gene and a linker or polylinker which are surrounded by the right and left T-DNA boundary region.

They can be transformed directly into the *agrobacteria*. The *agrobacterium* serving as a host cell shall contain a plasmid which carries a vir region. The vir region is necessary for the transfer of the T-DNA into the plant cell. Additional T-DNA may be present. The *agrobacterium* transformed in this way is used for transforming plant cells.

For transferring the DNA into the plant cell it is possible to co-cultivate vegetable explants usefully with *Agrobacterium tumefaciens* or *Agrobacterium rhizogenes*. Then, whole plants can be regenerated again from the infected plant material, e.g. leaf portions, stem segments, roots, protoplasts or suspension-cultivated plant cells in a suitable medium which may contain antibiotics of biocides for the selection of transformed cells. The resulting plants may then be tested for the presence of the introduced DNA. Other possibilities are known for introducing foreign DNA using the biolistic method or by protoplast fusion.

Alternative systems for transforming monocotyl plants are the transformation by means of the biolistic approach, the electrically or chemically induced DNA uptake in protoplasts, the electroporation of partially permeabilized cells, the macroinjection of DNA into inflorescence, the microinjection of DNA into microspores and pro-embryos, the DNA uptake by germinating pollen and the DNA uptake into embryos by swelling (for review: Potrykus, Physiol. Plant (1990), 269-273). While the transformation of dioctyl plants via Ti-plasmid vector systems by means of *Agrobacterium tumefaciens* is established, more recent studies point out that monocotyl plants are also accessible to transformation by means of vectors based on *agrobacterium*.

The transgenic host organisms useful for the method according to the invention may, in principle, be plants of any plant species, i.e. both monocotyl and dicotyl plants. Useful plants are preferred, in particular plants, such as wheat, barley, rice, corn, sugar beets, sugarcane, potatoes, brassicaceae, leguminous plants or tobacco. The plant portions desired for the expression of the desired protein or the treatment with the chemical inductors relate, in principle, to any plant portion, in any case to replication material and harvest products of these plants, e.g. fruit, seeds, nodules or bulbs, rootstocks, seedlings, cuttings, etc.

Furthermore, any protein, in particular a diagnostic protein, a therapeutic protein and/or a material protein, may be produced by the method according to the invention. The protein may originate from any individual, in particular humans or animals. The protein may also be present in wild-type or modified form. It may be a fusion protein or a protein fragment.

In a preferred embodiment, contacting with the chemical inductor is carried out in step (b) of the method according to the invention via the gas phase surrounding the host organism. This is done preferably by modifying the gas phase surrounding the host organism, i.e. the gas phase serves as a carrier for the induction stimulus, by atomizing an inductor solution, or by flooding using a volatile inductor. The modification of the gas phase in the host organism results preferably in an induction, e.g. of the promoter concerned. For physical reasons alone resulting from the utilization of the diffusion effect, a homogenous distribution of the induction stimulus is achieved after a certain time already. The period for reaching this homogenous distribution is considerably shortened by actively circulating the gas phase in the reaction chamber. Uniform and rapid penetration is thus achieved in particular in closely abutting cell substances as in plant leaves, algae or moss tissue. In particular in the case of compact tissues, e.g. potato tubers, the rapid tissue penetration according to the invention is of great advantage.

The person skilled in the art is familiar with suitable gaseous inductors as well as with conditions for an exchange of the gas phase as efficient as possible. Reference is made to the Anaerocult system (Merck, Darmstadt, Germany) which produces an anaerobic environment, in which oxygen is bound and $CO_2$ is released. In this system, the GapC4 promoter from corn is induced anaerobically by the $CO_2$ atmosphere (Bülow, L. et al., Molecular Plant-Microbe Interactions (1999), 182-188). The same effect is also achieved by introducing industrial nitrogen. Another example is the induction of "pathogenesis related protein" promoters, such as L-phenylalanine ammonium lyase promoters, chalcone synthase or "hydroyyproline rich glycoprotein" promoters by ethylene (Ecker, J. R. and Davis, R. W., Proc. Natl. Acad. Sci. USA 84 (1987), 5202-5206).

The person skilled in the art is also familiar with soluble inductors suitable for atomization and with conditions for an atomization as efficient as possible. Reference is made to a chimeric transcription-induction system which is induced by the soluble inductor dexamethasone (Plant J. 11 (1997) 605-612; Kunkel et al., Nature Biotechnol. 17 (1999), 916-918). The Incw1 promoter of corn is activated by the addition of sucrose of D-glucose (Chen, W. H. et al., Proc. Natl. Acad. Sci. U.S.A. 96 (1999), 10512-10517). Many "pathogenesis related protein" promoters are activated by salicylic acid (Gaffney et al., Nature 261 (1993), 754-756). A volatile inductor is methyl salicylate which is converted in the uptaking plant into salicylate which as described above has an inducing effect (Shulaev, V. et al., Nature 385 (1997), 718-721). The atomization of solutions, e.g. of promoter-inducing (bio)chemicals, offer the advantage of a technically simple and uniform distribution of the inducing substance around the tissue to be induced and into the tissue. A rapid and uniform distribution is preferably supported by an active circulation of the gas phase. In addition, a simple and efficient balance of resulting concentration differences is thus achieved, so that controlled process conditions can be guaranteed. In a particularly preferred embodiment, the agrochemical RH5992 (tebufenozide, Rohm & Haas, Croyden, U.K.) is used for the atomization, RH5992 functioning via a chimeric transcription activator protein as an inductor for the promoter to be induced (Gatz and Lenk, Trends in Plant Science 3 (1998), 352-358). The promoter is switched on specifically by RH5992 and is inactive without the presence of this compound. In this case, the inductor mist uniformly approaches the tissue to be induced by a continuous air distribution, for example. The active induction of the promoter is achieved by diffusion from the tissue surface into the cells.

Volatile inductors suitable for flooding and promoters inducible by them are also known to the person skilled in the art. In particular, methyl salicylate has to be mentioned which is converted in the uptaking plant into salicylate which, as described above, has an inducing effect (Shulaev, V. et al., supra). Another example of a volatile inductor is ethanol which induces the alcA promoter from *Aspergillus nidulans* in transgenic tobacco (Caddick, M. X., et al., Nature Biotechnology 16 (1998), 177-180). For active flooding one proceeds by flooding the liquid or solid (volatile) inductor with a suitable gaseous carrier medium for the purpose of conversion into the volatile gaseous phase and an active circulation of the gas phase is preferably carried out to obtain a uniform distribution of the inductor.

In a preferred embodiment, contacting with the chemical inductor takes place in step (b) of the method according to the invention via the liquid phase surrounding the host organism. This is done preferably via solutions of solid or liquid inducing (bio)chemicals. Reference is made to the above statements on the atomization of soluble inductors. It may be favorable to supply the chemical inductor via virus suspensions, e.g. the tobacco mosaic virus (TMV) in the case of tobacco, to the host organism, i.e. infect it therewith.

In a particularly preferred embodiment of the method according to the invention the gene coding for the desired protein is linked with an inducible promoter. Suitable promoters and the inhibitors in consideration for this (gaseous, liquid or solid, volatile compounds) are known to the person skilled in the art. They include e.g. the above described systems GapC4 promoter/$CO_2$ (Bülow et al., supra), the Adh1 promoter from corn/anaerobiosis (Ellis et al., EMBO J. 6 (1987), 11-16), the L-phenylalanine ammonium lyase promoters, chalcone synthase promoters or "hydroxyproline rich glycoprotein" promoters/ethylene (Ecker, J. R. and Davis, supra), the chimeric transcription induction system/dexamethasone (Plant J., supra), the Incw1 promoter from corn/sucrose or D-glucose (Chen, W. H. et al., supra), many "pathogenesis related protein" promoters/salicyclic acid or methyl salicylate (Gaffney et al. supra; Shulaev et al., supra), the alcA promoter from *Aspergillus nidulans* in transgenic tobacco/ethanol (Caddick, M. X. et al., supra).

The promoter is preferably a promoter inactive under aerobic conditions, such as the GapC4 prommoter of the Adh1 promoter, and induction takes place via a modification of the gas phase such that deoxidation is concerned. In this case, the aerobically inducible GapC4 promoter (DE 195 47 272) is particularly preferred, e.g. in combination with harvested transgenic plant tissue, e.g. transgenic potato tubers. Most vegetable promoters are switched off under anaerobic conditions while the GapC4 promoter is switched off under aerobic conditions and is switched on by simple deoxidation (Bülow et al., supra). This is achieved e.g. by introducing nitrogen or carbon dioxide into the reaction or storage space. Thus, a fully anaerobic environment is obtained within few hours even in an intact potato tuber so as to achieve promoter induction and foreign protein expression.

In another preferred embodiment of the method according to the invention, the expression of the gene coding for the desired protein is induced by compensating the functional inhibition of the transcription and/or translation. An example of a transcriptional inhibition is the HRT protein (repressor) from barley, which binds to the "gibberellinphytohormone response element" of the α-amylase promoter from barley (Raventos, D. et al., J. Biol. Chem. 273 (1998), 23313-23320). If this repressor is expressed under the control of the CaMV $^{35}$S promoter under aerobic conditions in a transgenic plant, it binds to the target sequence which is inserted between the gene coding for the desired protein and its promoter. If anaerobic conditions are produced, the 35S promoter is switched off and the repressor neosynthesis is stopped and hence the above gene is activated by the degradation of the existing repressor.

An example of the translational inhibition is the repression of the translation of the ferritin transcript in wheat germ extracts by the expression of a 90 kDa repressor from rat liver which binds to the 5'-untranslated region of the ferritin mRNA (Brown, P. H., J. Biol. Chem. 264 (1989), 13383-13386). The repressor of the ferritin mRNA is inserted before the cDNA sequence coding for the desired protein and the repressor is expressed in the transgenic plant.

The activity of the repressor may also be controlled directly by an inductor or inhibitor. For example, regulated transcriptional activation of the PS-IAA4/5 and PS-IAA6 promoters takes place in *Pisum sativum* by the addition of indoleacetic acid or cycloheximide, so that the trancript is not produced until these activators are present (Koshiba, T. et al., J. Mol. Biol. 253 (1995), 396-413). The translational repression of the tet operator is directly compensated in transgenic *arabidopsis* plants by e.g. adding tetracycline (Ulmasov, B. et al., Plant Mol. Biol. 35 (1997), 417-424).

In a particularly preferred embodiment, the method according to the invention is characterized in that the gene coding for the desired protein is functionally linked with a promoter such that a nucleic acid is inserted between the promoter and the gene, which is characterized in that (a) it prevents the transcription and/or translation of the gene; and (b) can be excised by means of induction, which results in the expression of the gene. Thus, the transcription or translation of the desired gene is prevented in the non-induced state and thus the foreign protein encoded by this gene does not form either. In an even more preferred embodiment of the method according to the invention, the inserted nucleic acid can be excised by a repressed and inducible recombinase. The gene coding for the recombinase may in this case be inserted separately in the host plant or may be localized itself on the inserted nucleic acid. A locally specific recombination and thus an excision of this nucleic acid sequence takes place only after activating the recombinase by a (bio)chemical physical or genetic inductor, and as a result the desired gene is localized directly downstream of the promoter, which initiates the transcription and translation and thus the foreign protein biosynthesis. As regards the inductors activating the recombinase reference is made to the above statements on the promoter induction systems. In particular it is mentioned that the recombinase gene may be located on the virus, e.g. TMV, and is not activated until the host organism has been infected.

The recombinase LBD system (WO 95/00555) is most preferred for the method according to the invention. It is inserted between the promoter and the foreign gene to be expressed as follows:

5'-promoter--R--recombinase LBD--R--foreign gene to be expressed--terminator-3'

(R=recombination site for recombinase LBD).

The recombinase is inactivated by fusion with the LBD domain. Having harvested the plant material, it is incubated with the inductor, e.g. estradiol, activating the foreign protein production and binding to the LBD domain. AS a result, the recombinase is activated and the cDNA fragment coding for recombinase is hence excised at both recombination sites and thus the gene to be expressed is localized directly downstream of the promoter. As a result, the transcription and translation of the gene to be expressed is thus enabled and the foreign protein is produced under controlled conditions.

Another alternative preferred embodiment of the method according to the invention is characterized in that the expression of the gene coding for the desired protein is made by compensating the effect of a transcriptional, post-transcriptional, translational or post-translational repressor, the separation of the repressor from the bound nucleic acid or protein sequence being induced by an external stimulus. Reference is made to the above statements on the compensation of the functional inhibition of transcription and/or translation.

Finally the present invention relates to a method in which various of the above described induction mechanisms are combined, e.g. as a two-component system. As a result, an even more restrictive regulation of the foreign gene expression, e.g. in transgenic plants, and thus an even more increased degree of biological safety can be achieved, at the same time it is possible to stop potential negative effects on the physiology of the plant. For example, a promoter inducible by a gaseous substance, e.g. the anaerobically inducible GapC4 promoter from corn, or a system based on a repressor can be combined with another system, e.g. a system based on recombination, so that the transcription of the respective foreign gene, based on the inducible promoter, is enabled only after combining promoter and gene by controlled recombination. For example, the above described recombinase LBD system (WO 95/00555) can be used as a recombination system, which consists of a 5' recombination site for the recombinase of the cDNA coding for the recombinase LBD protein and a 3' recombination site for the recombinase. In this two-component system, the promoter is inactive under aerobic conditions. The recombinase is also inactivated by the fusion with the LBD domain. Thus there is double repression. The foreign gene is therefore not expressed under agricultural and horticultural conditions, even if one of the two repression systems is not fully blocked by an environmental stimulus. This negative effect would then be absorbed by the second (repression) system). After the harvest of the plant material, the LBD domain-binding inductor is added for the foreign protein production and moreover aneanrobic conditions are established in the reaction chamber. This serves for activating the recombinase, on the one hand, and hence the cDNA fragment coding for recombinase is excised at the two recombination sites and thus the gene to be expressed is localized directly at the anaerobic promoter. Then, the transcription and translation of the gene to be expressed are enabled by producing anaerobic conditions and the foreign protein is produced under controlled conditions.

Another subject matter of the present invention relates to host organisms which contain the gene coding for the desired protein such that it is expressed only in the presence of a chemical inductor. The host organisms are in particular host organisms showing an above described transgenity. Corresponding reference is made to the above statements.

The following examples explain the invention.

EXAMPLE 1

Anaerobic Post-Harvest Production of scFv in Trangenic Potatoes

The anaerobically inducible GapC4 promoter (DE 195 47 272) was modified by means of a PCR reaction such that it contained at the 5' end a HincII restriction site and a NcoI restriction site. The following primer pair was used for the PCR reaction:

HincII-pGapC4 primer: CATGTCAACACATAAGGAA-GAAGAGGTAGAAAG (SEQ ID NO: 1) pGapC4-NcoI primer:

CATGCCATGGATCGATGACGGGGTTGGC-GAGTGTG (SEQ ID NO: 2)

The cDNA described by Artsaenko et al., Molecular Breeding 4 (1998), 313-319, which codes for an scFv antibody localized in the endoplasmic reticulum, was modified by means of a linker ligation (at the 5' end with CATGCCATGGCATG, (SEQ ID NO: 3) [5'-phosphorylated oligonucleotide]; at the 3' end with GCTCTAGAGC (SEQ ID NO: 4) [5'-phosphorylated oligonucleotide] such that it had an NcoI restriction site at the 5' end and an XbaI restriction site at the 3' end. The CaMV 35S promoter was removed from plasmid pRT100 (Töpfer et al. Nucleic Acids Research 15 (1987), 5890) by means of restriction digestion using HincII and XbaI. The two above described nucleic acid fragments which code for the GapC4 promoter and the scFv antibody, were inserted instead. After partial cleavage with HindIII, the expression cassette was isolated and inserted in the binary vector pSR 8-30 (Düring et al., Plant Journal 3, (1993), 587, 598; Porsch et al., Plant Molecular Biology 37 (1998), 581-585). The expression vector pSR 8-30/Gap-scFv(ox) was obtained.

It was used for transforming *E. coli* SM10 (Koncz and Schell, Molecular and General Genetics 204 (1986), 383-396). Transformants were mixed with *agrobacterium* GV 3101 (Koncz and Schell, supra) and incubated overnight at 28° C. (Koncz et al., Proc. Natl. Acad. Sci. U.S.A. 84 (1987), 131-135). Selection on carbenicillin was carried out, the bla gene necessary for this being present in the above expression vectors. Selection clones of *Agrobacterium tumefaciens* were applied onto cut off leaves, scratched several times at the middle rib, of a potato plant cv. Désirée, and the leaves were incubated in the dark for 2 days at 20° C. Thereafter, the *agrobacteria* were washed off and plant growth substances were added to the potato leaves, so that preferably shoots were regenerated. Furthermore, non-transformed cells were killed in the potato leaves by the addition of kanamycin (100 mg/ml) to the plant medium. Growing shoots were cut off and grew roots in the medium without plant growth substances but with kanamycin. The potato plants were further cultivated as usual.

For detecting the expression of the scFv antibody, cut-off leaf material or intact or cut-off bulb material was induced by means of the "Anaerocult" system (Merck, Darmstadt, Germany) as described by Bülow et al. (1999), supra. After 40 hours, the leaf material was removed and mortared. The detection of the expressed scFv antibody was made via the resulting c-myc Tag using the monoclonal antibody 9E10-IgG (Cambridge Research Chemicals, Northwich, Cheshire, U.K.) or protein L (Clontech, Palo Alto, Calif., U.S.A.) in a Western blot or ELISA. For this purpose, the whole protein of the potato material was isolated and used in the corresponding detection methods.

Transgenic potato plants determined to be expression-positive were cultivated in a greenhouse (in a pot or in a ground bed) or in the field under common horticultural or agricultural conditions. The tubers were harvested as usual and stored. For the post-harvest production of the scFv antibody, the tubers were placed in a reaction container made of steel (or plastics) which had a gas supply valve at its bottom and a gas discharge valve at its top. The air in the container was displaced rapidly by the industrial nitrogen (or carbon dioxide). A constant composition of the gas phase in the reaction container was adjusted in a slow gas stream (1 $m^3$ gas supply per hour per $m^2$ base area). After 40 hours, the tubers were taken out of the reaction container, homogenized, the solids content was centrifuged off and the aqueous supernatant was supplied for chromatographic purification of the scFv antibody. By a comparison of samples before and after the deoxidation it could be shown that no scFv antibody was produced before the oxygen was displaced and significant amounts thereof were produced after the displacement.

EXAMPLE 2

Recombination-Mediated Post-Harvest Production in Transgenic Potatoes

The cDNA described in Artsaenko et al. (1998) which codes for an scFv antibody localized in the endoplasmic reticulum, was modified by means of a linker ligation as described in Example 1, such that it had an NcoI restriction site at the 5' end and an XbaI restriction site at the 3' end. This nucleic acid sequence was inserted in the plasmid pRT100 in the polylinker sequence. The plasmid pRT100/scFv(ox) was obtained. A synthetic nucleic acid was inserted in the NcoI restriction site of pRT100/scFv(ox) which contains two FRT recombination sites (Buchholz et al., Nucleic Acids Res. 24 (1996), 3118-3119). The plasmid pRT 100/FRT-scFv(ox) was obtained. The cDNA coding for the FLP-recombinase LBD fusion protein (WO 95/00555) was inserted as PCR-adapted NcoI-XbaI fragment in the NcoI cleavage site of pRT 100 in the sense orientation behind the CaMV $^{35}$S promoter (Odell et al., Nature 313 (1985), 810-812) (plasmid pRT 100/FLP). The following primer pair was used for this purpose:

NcoI-PLP-LBD primer: CATGCCATGCCA-CAATTTGATATATTATGTAAAAC (SEQ ID NO: 5)

FLP-LBD-XbaI primer: GCTCTAGATCAGACTGTG-GCAGGGAAACCCTC (SEQ ID NO: 6)

The expression cassette from pRT 100/FLP was inserted as partially digested PstI fragment between the two FRT recombination sites. As a result, the plasmid pRT 100/rec-scFv(ox) was obtained.

Following cleavage with HindIII the expression cassette from pRT 100/rec-scFv(ox) was isolated and inserted in the binary vector pSR 8-30 (Düring et al., Plant Journal 3 (1993), 587-598; Porsch et al., Plant Molecular Biology 37 (1998), 581-585). The expression vector pSR 8-30/rec-scFv (ox) was obtained. Transgenic potato plants were produced as described in Example 1.

For detecting the expression of the scFv antibody, in vitro cultivated potato plants were reacted on a medium with $10^{-6}$ M estradiol (Sigma Chemicals, St. Louis, Mo., U.S.A.) and cultivated for 2 days. Thereafter, the plant material was harvested and mortared. The detection of expressed scFv antibodies was again made via the contained c-myc Tag (cf. supra) or protein L in Western blot or ELISA. For this purpose, the whole protein of the potato material was isolated and used in the corresponding detection methods.

Potato plants of lines determined to be expression positive were removed from the clonal in vitro culture and planted out in a greenhouse. These individual plants had not yet been treated with estradiol so that no recombination had taken place yet. Likewise the cultivation in the field was made under common agricultural conditions. The tubers were harvested as usual and stored. For the post-harvest production of the scFv antibody the tubers were incubated with an atomized solution of $10^{-6}$ M estradiol in a reaction container. The technical realization was as described in above Example 1. After 40 hours, the tubers were removed from the reaction container, homogenized, the solids content was centrifuged off and the aqueous supernatant was supplied to the chromatographic purification of the scFv antibody. By comparing samples before and after they were contacted with estradiol it could be shown that no scFv antibody was produced before the samples were contacted with estradiol, but thereafter significant amounts thereof were produced.

The invention claimed is:

1. A method for obtaining a protein from a transgenic host potato plant, wherein the gene coding for said protein is not expressed until said transgenic host potato plant has been harvested, said method comprising the steps of:
   a) obtaining a transgenic host potato plant comprising a gene coding for a protein wherein said gene is functionally linked to an anaerobically inducible promoter and said gene is only expressed upon anaerobic induction;
   b) cultivating said transgenic host potato plant;
   c) harvesting said transgenic host potato plant thereby obtaining harvested transgenic host potato plant tissue;
   d) transferring said harvested transgenic host potato plant tissue into a reaction container;
   e) displacing a gas phase in said reaction container by introducing a gaseous inductor selected from the group consisting of nitrogen and carbon dioxide into said reaction container, thereby producing anaerobic conditions;

f) expressing said protein in said harvested transgenic host potato plant tissue by anaerobic induction of said anaerobically inducible promoter; and g) recovering said protein expressed in step f) from said harvested transgenic host potato plant tissue.

2. The method of claim 1, wherein said promoter is GapC4 or Adh1 promoter.

* * * * *